(12) United States Patent
McFarlane

(10) Patent No.: US 9,901,373 B2
(45) Date of Patent: *Feb. 27, 2018

(54) CAGED FLOATING SEAL ASSEMBLY

(71) Applicant: Teleflex Medical Incorporated, Durham, NC (US)

(72) Inventor: Richard H. McFarlane, Rivera Beach, FL (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 63 days.

This patent is subject to a terminal disclaimer.

(21) Appl. No.: 14/339,840

(22) Filed: Jul. 24, 2014

(65) Prior Publication Data
US 2014/0336584 A1 Nov. 13, 2014

Related U.S. Application Data

(63) Continuation of application No. 12/790,164, filed on May 28, 2010, now Pat. No. 8,821,445, which is a
(Continued)

(51) Int. Cl.
A61B 17/34 (2006.01)
A61M 39/06 (2006.01)
A61B 17/00 (2006.01)

(52) U.S. Cl.
CPC ..... *A61B 17/3462* (2013.01); *A61M 39/0613* (2013.01); *A61B 2017/00876* (2013.01);
(Continued)

(58) Field of Classification Search
CPC .. A61M 2039/0633; A61M 2039/0686; A61M 2039/062; A61M 39/06; A61M 39/0606; A61M 2039/064; A61M 2039/0653; A61M 2039/0626; A61M 25/0668; A61M 2039/0646; A61M 2039/066; A61M 2039/0673; A61M 2039/0666; A61M 39/0613;
(Continued)

(56) References Cited

U.S. PATENT DOCUMENTS 3,313,299 A 4/1967 Spademan
4,149,535 A 4/1979 Voider
(Continued)

FOREIGN PATENT DOCUMENTS

JP 2004-283592 10/2004
WO WO2003091608 11/2003

Primary Examiner — Kevin C Sirmons
Assistant Examiner — William Carpenter
(74) Attorney, Agent, or Firm — Baker and Hostetler LLP

(57) ABSTRACT

A seal assembly establishes sealing engagement with a plurality of differently dimensioned instruments passing through a trocar. The seal assembly is a caged seal assembly movably disposed within the trocar and includes at least two seal segments disposable into and out of a sealing orientation relative to the instrument. A cage structure of the seal assembly includes at least two cage segments each connected to a seal segment, a biasing assembly connected to the cage structure and disposed and structured to normally bias the seal segments into sealing orientation.

15 Claims, 22 Drawing Sheets

Related U.S. Application Data continuation of application No. 11/892,814, filed on Aug. 27, 2007, now Pat. No. 7,731,695.

(60) Provisional application No. 60/840,174, filed on Aug. 25, 2006, provisional application No. 60/852,583, filed on Oct. 18, 2006.

(52) U.S. Cl.
CPC ............... *A61B 2017/3464* (2013.01); *A61M 2039/0626* (2013.01); *A61M 2039/0653* (2013.01); *A61M 2039/0686* (2013.01)

(58) Field of Classification Search
CPC .............. A61M 39/0693; A61M 39/26; A61B 17/3462; A61B 2017/3464; A61B 17/3498; A61B 2017/3419
See application file for complete search history.

(56) References Cited

U.S. PATENT DOCUMENTS

| | | | |
|---|---|---|---|
| 4,177,814 A | 12/1979 | Knepshield et al. | |
| 4,351,328 A | 9/1982 | Bodai | |
| 4,430,081 A | 2/1984 | Timmermans | |
| 4,475,548 A | 10/1984 | Muto | |
| 4,484,916 A | 11/1984 | McPhee | |
| 4,601,710 A | 7/1986 | Moll | |
| 4,626,245 A * | 12/1986 | Weinstein | A61M 39/0606 137/849 |
| 4,634,424 A | 1/1987 | O'Boyle | |
| 4,654,030 A | 3/1987 | Moll et al. | |
| 4,673,393 A | 6/1987 | Suzuki et al. | |
| 4,917,668 A | 4/1990 | Haindl | |
| 4,929,235 A * | 5/1990 | Merry | A61M 39/0606 137/849 |
| 4,978,341 A | 12/1990 | Niederhauser | |
| 5,030,206 A | 7/1991 | Lander | |
| 5,104,383 A | 4/1992 | Shichman | |
| 5,108,380 A | 4/1992 | Herlitze et al. | |
| 5,114,408 A | 5/1992 | Fleischhaker et al. | |
| 5,127,626 A | 7/1992 | Hilal et al. | |
| 5,141,498 A | 8/1992 | Christian | |
| 5,167,636 A | 12/1992 | Clement | |
| 5,167,637 A | 12/1992 | Okada et al. | |
| 5,197,955 A | 3/1993 | Stephens et al. | |
| 5,209,737 A * | 5/1993 | Ritchart | A61B 17/3462 604/167.03 |
| 5,242,409 A | 9/1993 | Buelna | |
| 5,269,764 A | 12/1993 | Vetter et al. | |
| 5,299,813 A | 4/1994 | McKenna | |
| 5,308,336 A | 5/1994 | Hart et al. | |
| 5,312,362 A | 5/1994 | Pfolsgraf et al. | |
| 5,338,307 A | 8/1994 | Stephens et al. | |
| 5,342,315 A * | 8/1994 | Rowe | A61B 17/3462 604/167.06 |
| 5,342,316 A | 8/1994 | Wallace | |
| 5,344,420 A | 9/1994 | Hilal et al. | |
| 5,350,364 A | 9/1994 | Stephens et al. | |
| 5,385,553 A | 1/1995 | Hart et al. | |
| 5,389,080 A | 2/1995 | Yoon | |
| 5,391,153 A | 2/1995 | Haber et al. | |
| 5,407,433 A | 4/1995 | Loomas | |
| 5,411,483 A | 5/1995 | Loomas et al. | |
| 5,429,598 A | 7/1995 | Waxman et al. | |
| 5,429,609 A | 7/1995 | Yoon | |
| 5,443,452 A | 8/1995 | Hart et al. | |
| 5,453,095 A | 9/1995 | Davila et al. | |
| 5,456,284 A | 10/1995 | Ryan et al. | |
| 5,476,475 A | 12/1995 | Gadberry | |
| 5,496,280 A | 3/1996 | Vandenbroek et al. | |
| 5,540,661 A | 7/1996 | Tomisaka et al. | |
| 5,545,142 A | 8/1996 | Stephens et al. | |
| 5,569,205 A | 10/1996 | Hart et al. | |
| 5,584,850 A | 12/1996 | Hart et al. | |
| 5,603,702 A | 2/1997 | Smith et al. | |
| 5,618,297 A | 4/1997 | Hart et al. | |
| 5,628,732 A | 5/1997 | Antoon, Jr. et al. | |
| 5,634,908 A | 6/1997 | Loomas | |
| 5,645,076 A | 7/1997 | Yoon | |
| 5,651,771 A | 7/1997 | Tangherlini et al. | |
| 5,657,963 A | 8/1997 | Hinchliffe et al. | |
| 5,709,664 A | 1/1998 | Vandenbroek et al. | |
| 5,720,730 A | 2/1998 | Blake, III | |
| 5,720,759 A | 2/1998 | Green et al. | |
| 5,782,812 A | 7/1998 | Hart et al. | |
| 5,782,817 A | 7/1998 | Franzel et al. | |
| 5,788,676 A | 8/1998 | Yoon | |
| 5,792,113 A | 8/1998 | Kramer et al. | |
| 5,803,919 A | 9/1998 | Hart et al. | |
| 5,814,026 A | 9/1998 | Yoon | |
| 5,820,600 A | 10/1998 | Carlson et al. | |
| 5,827,228 A | 10/1998 | Rowe | |
| 5,913,847 A | 6/1999 | Yoon | |
| 5,916,198 A | 6/1999 | Dillow | |
| 5,916,232 A | 6/1999 | Hart | |
| 5,984,919 A | 11/1999 | Hilal et al. | |
| 5,989,224 A | 11/1999 | Exline et al. | |
| 5,989,232 A | 11/1999 | Yoon | |
| 5,989,233 A | 11/1999 | Yoon | |
| RE36,702 E | 5/2000 | Green et al. | |
| 6,083,207 A * | 7/2000 | Heck | A61M 39/06 604/160 |
| 6,123,689 A | 9/2000 | To et al. | |
| 6,159,182 A | 12/2000 | Davis et al. | |
| 6,228,061 B1 | 5/2001 | Flatland et al. | |
| 6,258,065 B1 | 7/2001 | Dennis et al. | |
| 6,276,661 B1 | 8/2001 | Laird | |
| 6,402,723 B1 | 6/2002 | Lampropoulos et al. | |
| 6,416,499 B2 | 7/2002 | Paul, Jr. | |
| 6,482,181 B1 | 11/2002 | Racenet et al. | |
| 6,551,283 B1 | 4/2003 | Guo et al. | |
| 6,699,221 B2 | 3/2004 | Vaillancourt | |
| 7,011,314 B2 | 3/2006 | McFarlane | |
| 7,112,185 B2 | 9/2006 | Hart et al. | |
| 7,731,694 B2 | 6/2010 | Becker et al. | |
| 2003/0181865 A1 | 9/2003 | Abrahamson et al. | |
| 2005/0283165 A1 | 12/2005 | Gadberry | |
| 2007/0106262 A1 | 5/2007 | Becker et al. | |
| 2007/0185453 A1 | 8/2007 | Michael et al. | |

\* cited by examiner

CAGED FLOATING SEAL ASSEMBLY

CROSS-REFERENCE TO RELATED APPLICATIONS

This application claims priority to, and is a continuation of, pending U.S. application Ser. No. 12/790,164, filed May 28, 2010, which is a continuation of, U.S. application Ser. No. 11/892,814, filed Aug. 27, 2007, now issued as U.S. Pat. No. 7,731,695, which claims priority to U.S. Provisional Application No. 60/840,174, filed Aug. 25, 2006, now expired and U.S. Provisional Application No. 60/852,583, filed Oct. 18, 2006, now expired. This application claims priority to each of the above mentioned applications and the disclosure of each above mentioned application is hereby incorporated by reference in its entirety.

FIELD OF THE INVENTION

The present invention relates generally to medical devices. More particularly, the present invention relates to seal assemblies for trocars and like instruments.

BACKGROUND OF THE INVENTION

This invention relates to a caged seal assembly that is floatingly movable within a trocar or like device and intended for use independently of, but preferably, in combination with another seal assembly, which is also floatingly movable within the trocar. As such, a variety of medical instruments can be utilized with the present invention, so as to introduce and/or access the body cavity of a patient, regardless of the fact that each instrument may have a differently sized outer diameter, which would typically fall into a range of generally about 5 mm to 12 mm. Moreover, the caged seal assembly is structured to automatically assume either a non-sealing orientation or a sealing orientation, dependent at least in part on the size of the instrument passing through the trocar assembly.

Laparoscopic surgery has become quite common in recent years as it generally avoids several significant drawbacks associated with previous surgical methods. Those methods involved the making of large incisions into a patient's body so as to give the surgeon clear and unobstructed visual access to the targeted organ(s) or anatomical tissue of the patient for the surgical procedure involved.

In stark contrast, the currently favored surgical technique of laparoscopy involves the forming one or more small entry sites in the patient's abdominal wall for accessing his or her body cavity, using a trocar or like device to provide a working channel, and performing surgery on the targeted organ(s) or tissue via a medical instrument inserted into the trocar or like device. Following this type of surgery, patients usually experience significantly less pain and recover much more quickly than when the older surgical methods were used, and as a result, the minimally invasive procedures of laparoscopy have become well accepted in the medical field.

The trocar used in performing laparoscopic surgery typically includes an elongated tube or cannula, and the formation of the small surgical entry site(s) usually involves the insertion of an obturator with a sharp distal tip within the trocar and then pushing through the abdominal tissues until the wall or thick lining of the abdominal cavity is punctured. There are other techniques for making what is known as this "first stick" that do not involve using an obturator with a very sharp tip, as these can inflict damage by inadvertently nicking or puncturing an organ during insertion. Regardless, once the abdominal cavity has been reached, the obturator is usually removed from the trocar cannula, whereupon the abdominal cavity is inflated with a suitable gas, such as carbon dioxide, to provide space within the abdomen for the surgery to take place. The trocar cannula or like device remains in place at the entry site(s) and functions as a working channel across the abdominal tissues and thick lining of the abdominal cavity, and into that cavity, such that relatively thin and long handled instruments, including forceps, scissors, retractors, dissectors, etc., as well as a tiny video camera and light source, which are all specifically designed for this purpose, may be inserted through the trocar, although there will often be more than one trocar in place during surgery. While positioned in a trocar, the chosen medical instruments are manipulated by the surgeon into contact with the patient's organ(s) or anatomical tissue involved in the procedure.

As noted above, during laparoscopy the patient's abdominal cavity is typically insufflated, usually by the attachment of a source of gas to the trocar assembly, which gas is forced under pressure into the accessed abdominal cavity. Once that cavity is inflated, it is important that the fluid pressure within the body cavity be maintained in order to provide the needed access to the internal organs, as well as adequate room for visual observation during the surgical procedure. Therefore, it is important to prevent the escape of pressurized fluid from within the body cavity, back through the cannula and/or housing associated with the trocar. This is commonly achieved by the use of valves or sealing mechanisms within the trocar, and both "septum" valves and "zero closure" valves are used for this purpose. For example, it is known to use "septum" valves located at the proximal end of the trocar, usually within the housing of the trocar, to form a seal around the outer surface of a medical instrument which has been inserted within the trocar. However, these types of seals will not usually prevent the escaping of gas once a medical instrument has been removed from the trocar. As such, it is also known to provide trocars with a "zero closure" valve to prevent gas from escaping when there is no medical instrument present within the trocar.

First, and as indicated above, laparoscopic surgery can involve a variety of medical instruments during any given surgical procedure and there are also a number of manufacturers of such instruments. Accordingly, among other things, the outer diameters of these medical instruments can and do vary. For example, it is quite common for the outer diameters of such medical instruments to vary within a conventionally current range from about 3 mm to 15 mm.

This fact, however, presents an obstacle for preventing the escape of gas by a septum-type valve because such valves typically accommodate and effectively seal against medical instruments having a comparatively small and relatively limited range of outer diameters. This limited effective dimensional range may cause some disruption in the performance of the surgery. For example, the septum valve seal will not perform adequately when a medical instrument having a smaller outer diameter than the set size offered by the septum valve must be used. During such an occurrence there is a strong possibility that some insufflation gas will escape thereby necessitating the abdominal cavity being inflated again. As another example, if a medical instrument having a much larger outer diameter which is beyond the size of the valve within the trocar, there may be an unacceptable drag or friction force exerted on the instrument during its insertion into or removal from the trocar and/or while its is being manipulated during surgery. Further, the septum valve may become ripped, torn or otherwise damaged, leading to a loss of insufflation gas and/or a need to replace the trocar, etc. during surgery.

Known attempts to solve these problems have resulted in the provision of attachment devices for the trocar, which provide another or supplemental septum valve to accommodate the use of medical instruments having differently sized outer diameters during surgery. However, such devices must still be manipulated and/or somehow attached to the trocar to permit use during surgery. The required manipulation of them also has a tendency to interrupt the surgical procedures, at least somewhat, and further, can prove to be cumbersome and/or challenging, especially if the hands of the medical personal are wet, bloodied, slippery, etc.

In addition and as also noted above, during at least some laparoscopic procedures the trocar remains inserted through the patient's abdominal wall and into the abdominal cavity, so as to act as the working channel into which the various medical instruments are inserted or removed. However, during such procedures, the trocars are often disposed or manipulated to assume various angles such as an angularly, off-set position relative to the trocar. As such, the instrument could well be disposed out of axial alignment with the central axis of the trocar housing, as well as any septum valve or other valve assembly associated therewith. Again, the undesirable result may be a disruption in the performance of the surgery. Further by way of example, known septum valves are commonly made of a very thin, flexible material which can be punctured or ripped when a medical instrument is inserted at a skewed angle. This, in turn, can result in the loss of insufflation gas during surgery and a resulting delay if the trocar must be replaced. Also, while a surgery is in progress the manipulation of medical instruments within the trocar has been known to cause the septum valves to become "egg-shaped" which also typically results in the loss of some insufflation gas. Despite the recognition of these and other disadvantages and problems and the numerous attempts to address them, there remains an appreciable need for an improved mechanism or assembly for sealing the outer surface of medical instruments used in trocars or like devices. Any such improved sealing mechanism should be suitable for and readily used with a trocar assembly or like device, and further, should effectively maintain insufflation pressure within a patient's body cavity, once it has been accessed and inflated. Any such improved sealing mechanism should also accommodate and/or facilitate the introduction of medical instruments into the trocar, even when oriented in an angular, off center orientation relative to the longitudinal axis of the trocar and/or the inlet port associated therewith, and should also resist the formation of ovals or "egg-shapes," especially when the medical instrument is being forcibly manipulated and otherwise used during surgery.

Further, any such improved sealing mechanism should be structured to prevent or significantly reduce the possibility of damage thereto, especially when the seal assembly comes into contact with the distal end of a medical instrument being introduced. Any such improved sealing mechanism should also be capable of accommodating a number of medical instruments of various outer diameters, such as, but not limited to, those falling within a currently conventional range of about 3 mm to 15 mm. Ideally, any such improved sealing mechanism would also accomplish all of the foregoing without creating excessive drag or friction on the medical instrument while it is being inserted into or removed from a trocar or otherwise moved about during performance of a surgery.

SUMMARY OF THE INVENTION

The foregoing needs are met, to a great extent, by the present invention, wherein in one aspect an apparatus is provided that in some embodiments provides a caged seal assembly which establishes sealing engagement with a plurality of differently dimensioned instruments passing through a trocar. The seal assembly is a caged seal assembly movably disposed within the trocar and includes at least two seal segments disposable into and out of a sealing orientation relative to the instrument. A cage structure of the seal assembly includes at least two cage segments each connected to a seal segment, a biasing assembly connected to the cage structure and disposed and structured to normally bias the seal segments into sealing orientation.

In accordance with one embodiment of the present invention, a seal assembly is structured to establish sealing engagement with differently dimensioned instruments passing through a trocar. A caged seal assembly is movably disposed within the trocar in receiving relation to an instrument passing therethrough. The caged seal assembly includes at least two seal segments disposable into and out of a sealing orientation relative to the instrument. The caged seal assembly is dimensioned and configured to establish sealing engagement with instruments within a predetermined dimensional range. A cage structure including at least two cage segments each connected to a different one of said seal segments, a biasing assembly is connected to the cage structure and disposed and structured to normally bias said seal segments into said sealing orientation. The cage structure and the biasing assembly are cooperatively structured to dispose said seal segments out of said sealing orientation upon passage therethrough of an instrument sized greater than said predetermined dimensional range.

In accordance with another embodiment of the present invention, a seal assembly is provided for sealing engagement with differently dimensioned instruments passing through a trocar. A caged seal assembly includes a plurality of caged segments movably connected to one another. The caged seal assembly includes a plurality of seal segments each connected to a different one of said cage segments and movable therewith between a sealing orientation and a non sealing orientation relative to an instrument passing through said caged seal assembly. A biasing assembly is connected to said cage segments and disposed and structured to normally bias said seal segments into said sealing orientation. At least some of said cage segments include a guide portion formed of a material having a predetermined rigidity and disposed in an exposed position relative to an instrument passing through said caged seal assembly. The plurality of cage segments and the biasing assembly are cooperatively structured to facilitate disposition of said seal segments out of said sealing orientation upon passage therethrough of an instrument having a predetermined greater size than said predetermined dimensional range.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
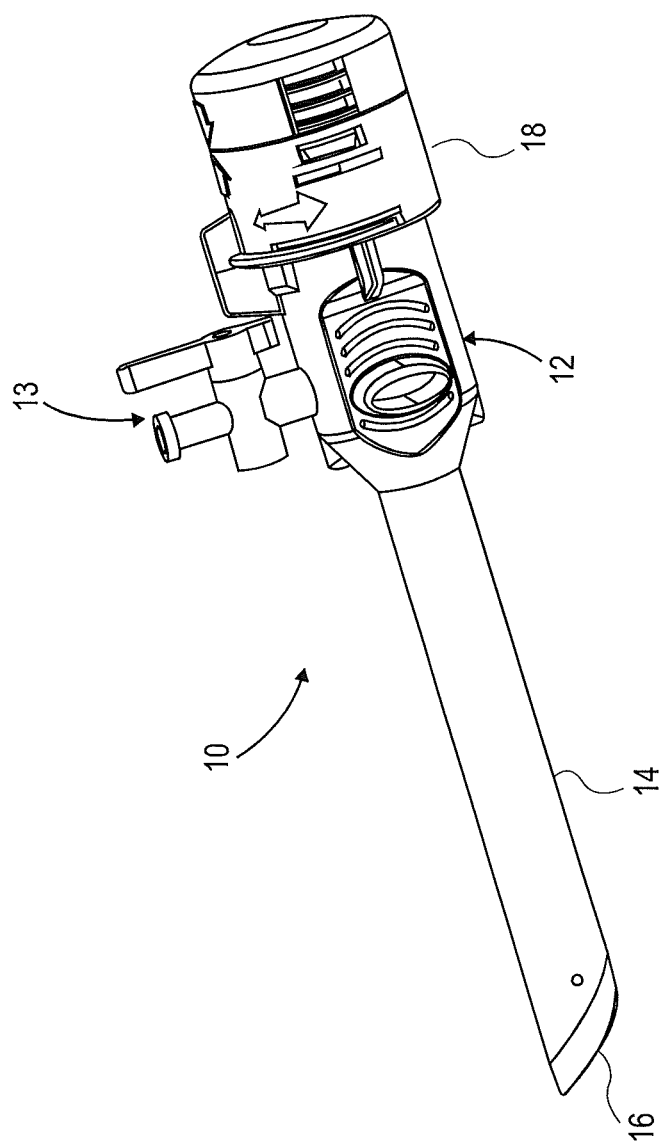
FIGS. 1 and 1A are perspective views of representative types of trocar assemblies with which various preferred embodiments of the seal assembly of the present invention may be used.

The present invention is intended to present a solution to these and other long felt needs in this field of art, and as such, relates to a seal assembly including a caged seal assembly primarily structured to be used with a trocar or like device. The caged seal assembly is operational independent of, but preferably in combination with, an additional seal assembly, also defining a preferred embodiment of the present invention, and disposed along a common instrument path within the trocar. As such, the combined caged seal assembly and the additional seal assembly facilitates the sealed passage of medical instruments through the trocar, so as to prevent the escape of insufflation gas such as during laparoscopic surgery. The seal assembly of the present invention is directed to what is accurately and descriptively referred to herein as a movable or "floating" and/or "caged" seal assembly, the features of which are discussed in detail hereinafter.

More specifically, the various preferred embodiments of the seal assembly of the present invention are structured to establish sealing engagement with any one of a plurality of differently dimensioned medical instruments passing through a trocar, wherein the instruments and the trocar are of the type commonly used in laparoscopic surgery. As set forth herein, the seal assembly of the present invention comprises a caged seal assembly movably, or more specifically, "floatingly" disposed within the trocar along an intended path of travel of an instrument passing through the trocar and in receiving relation to that instrument.

The caged seal assembly includes a plurality of seal segments, preferably two in number, which can be "automatically" disposable into and out of a sealing orientation with the exterior surface of the instrument passing through the trocar and through the caged seal assembly. As will be described in greater detail hereinafter, the sealing orientation of the caged seal assembly comprises the two seal segments collectively disposed in engaging and surrounding relation to an instrument passing there through. When the seal segments are so positioned, a substantially fluid tight seal is formed about the corresponding exterior surface of an instrument, having an outer diameter of an appropriate size, thereby preventing or significantly reducing the possibility of the escape of insufflation gas used in the aforementioned laparoscopic surgery.

In order to facilitate disposition and maintenance of the seal segments in the aforementioned sealing orientation, the caged seal assembly of the present invention includes a cage structure including a plurality of preferably, at least two cage segments. Each of the cage segments is connected to a different one of the preferably two seal segments in a substantially fixed manner so as to be movable therewith. Accordingly, both the seal segments and corresponding ones of the cage segments connected thereto are concurrently movable into either a sealing orientation or a non sealing orientation dependent, at least in part, on the size of the instrument passing through the caged seal assembly.

In order to accomplish the substantially "automatic" disposition of the caged seal assembly between the sealing orientation and the non-sealing orientation, the present invention further includes a biasing assembly. The biasing assembly is connected to the cage structure and disposed and structured to normally bias the seal segments, by virtue of their being connected to the seal segments, into the aforementioned sealing orientation. The structure and disposition of the biasing assembly is such as to normally bias the cage segments and the corresponding seal segments attached thereto into a "closed" position, thereby allowing the seal segments to assume the sealing orientation. However, the various embodiments of the biasing assembly and present inventive apparatus facilitate the disposition of the seal segments and the cage segments attached thereto into the aforementioned non-sealing orientation, such as when a large instrument forced through the caged seal assembly.

More specifically, the disposition of the caged seal assembly in the non-sealing orientation is a result of an instrument passing through the trocar, along the intended instrument path of travel, such that the instrument will pass through and/or between the seal segments. However, the caged seal assembly of the present invention is specifically dimensioned, configured and structured to establish sealing engagement, and thereby assume the sealing orientation with any one of a plurality of instruments which are sized to be within a predetermined dimensional range such as, but not limited to, between generally about 3 mm and generally about 5 mm. If a significantly larger instrument attempts to pass through the caged seal assembly, the biasing assembly associated with the cage structure will allow an opening or separation of the seal segments out of the sealing orientation and into what is referred to as the non-sealing orientation. However, upon removal of the larger instrument from the caged seal assembly, the biasing assembly connected to or otherwise associated with the cage structure is arranged, structured or configured to force or bias the cage segments back into a closed configuration. The closed configuration of the cage segments forces or biases the seal segments back into a sealing orientation so as to again be disposed to receive and sealingly engage an appropriately dimensioned instrument which passes through the trocar.

As set forth above, a preferred embodiment of the seal assembly of the present invention comprises the caged seal assembly being operatively disposed on or within a trocar structure in combination with a supplementary or additional seal assembly. As such, the seal assembly of the present invention demonstrates a greater versatility by establishing a sealing engagement with any one of a plurality of instruments having an increased dimensional range than that for which the caged seal assembly may be dimensioned, configured or structured.

Moreover, the versatility of the seal assembly of the present invention is significantly enhanced by virtue of the establishment of sealing engagement with the exterior surface of various instruments passing through the trocar which have both relatively small and relatively large dimensions. As set forth above, the caged seal assembly may be structured to establish sealing engagement with relatively small instruments such as, but not limited to, a dimensional range of generally about 3 mm to generally about 5 mm. However, during a typical laparoscopic surgical procedure, the medical personnel may require the need or use of a significantly larger instrument, such as, but not limited to, a dimensional range of generally about 10 mm to generally about 15 mm. Utilization of a larger instrument having a dimensional range, larger than that intended for use with the caged seal assembly, would normally cause significant drag and/or frictional engagement being exerted on the instrument as it passes through the caged seal assembly and/or is manipulated by the medical personnel during the surgical procedure.

Accordingly, such problems are overcome by the provision of the additional or supplementary seal assembly and the ability of the caged seal assembly to "automatically" assume the non-sealing orientation, wherein it is disposed out of sealing engagement with the larger instrument passing there through. When the seal is in the non-sealing orientation it adds very little friction to the sealing system when a larger instrument is inserted. More specifically, the additional seal assembly is disposed, dimensioned, configured and structured to establish sealing engagement with an instrument having a larger dimensional range, such as, but not limited to, the aforementioned 10 mm to 15 mm range. Therefore, when such a larger instrument is passed into the trocar, sealing engagement is established between the additional seal assembly and the larger instrument. Further, the additional seal assembly is located along a common, intended path of travel of the instrument as is the caged seal assembly. Therefore, when the larger instrument passes into and through the caged seal assembly, cooperative structuring and disposition between the cage structure and biasing assembly will allow an opening or separation of the two seal segments such that they will be "forced" out of a normal sealing orientation. Moreover, positioning and manipulation of the larger instrument will be facilitated by virtue of the establishment of sealing engagement between the additional or supplementary seal and the exterior surface of the larger instrument.

This established sealing engagement will be sufficient to eliminate or significantly reduce the escape of insufflation gas even though the caged seal assembly is not disposed in a sealing orientation relative to the exterior surface of the larger instrument. It is emphasized that the caged seal assembly and the additional or supplementary seal assembly are intended to establish sealing engagement with generally differently sized instruments. However, it should be recognized that there may be a dimensional range of instruments that may be sealed by both the caged seal assembly and the additional seal assembly. In the examples described herein, the dimensional range of such instruments would be somewhat larger than generally about 5 mm and somewhat smaller than generally about 10 mm.

The function and operation of the seal assembly, when the caged seal assembly is used independently of or in combination with the additional seal assembly is significantly enhanced by movably and more specifically floatingly disposing both the caged seal assembly and the additional seal assembly on or within the trocar and along a common path of travel or passage of an instrument passing through the trocar. Such floating movement facilitates the maintenance of a sealing engagement with one or both of the caged seal assembly and/or additional seal assembly with an instrument passing there through even when the instrument, due to manipulation during the surgical procedure, is orientated at a severe angled or skewed orientation.

These and other objects, features and advantages of the present invention will become more clear when the drawings as well as the detailed description are taken into consideration, in which like reference numerals refer to like parts throughout.

Figure 1A:
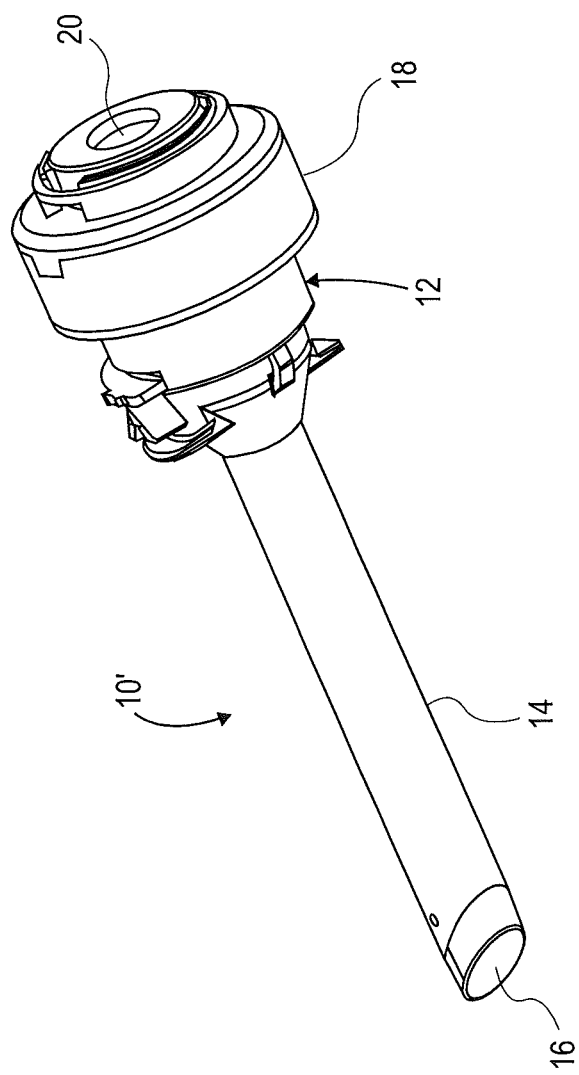

FIGS. 1 and 1A are representative trocar structures with which the seal assembly of the present invention may be utilized. However, as emphasized herein, the various preferred embodiments of the seal assembly of the present invention are not intended to be limited for use with a single type of trocar. Accordingly, for purposes of clarity the representative trocar assemblies are generally indicated as 10 and 10' and each include a housing 12 having at least partially hollow interiors dimensioned and configured to include various valving and/or sealing structures. In addition, the housing 12 may include one or more inlet ports or valves generally indicated as 13 structured to introduce and/or remove insufflation gas. When introduced into the trocar, the insufflation gas passes into the housing 12, along an elongated barrel or cannula 14 and out through the open distal end 16 of the cannula 14. As is also common surgical practice, the trocar and in particular the open end 16 and the barrel 14 will penetrate the body of the patient, such as by employing an obturator of some type assembled with the cannula, and enter the abdominal cavity or other area in which the laparoscopic surgery is to be performed. In addition, each of the representative trocar assemblies 10 and 10' include an end portion generally indicated as 18, which may be a part of the respective trocar assemblies 10 and 10' or may be removably or otherwise attached thereto in operative position.

As best represented in FIG. 1A, the portion 18 may include an inlet or like opening 20 for the introduction of one or more individual instruments into the interior or the trocar housing so as to facilitate its passage along the interior of the cannula 14 for eventual entry into the body cavity of the patient. As the instrument passes through the housing 12 and/or end portion 18 it will engage one or more sealing structures which prevent or significantly reduce the escape of insufflation gas commonly used in laparoscopic surgery for the expansion of the body cavity in which the surgical procedure is being performed. With specific relation to the seal assembly 30 of the present invention, which is described in greater detail hereinafter, its placement will be located within an appropriate portion of the housing 12 and/or end portion 18. Also the seal assembly 30 will be disposed along an intended path of travel of the instrument as it passes into the inlet or opening 20, through the housing 12, end portion 18 and along the length of the cannula 14.

Figure 2:
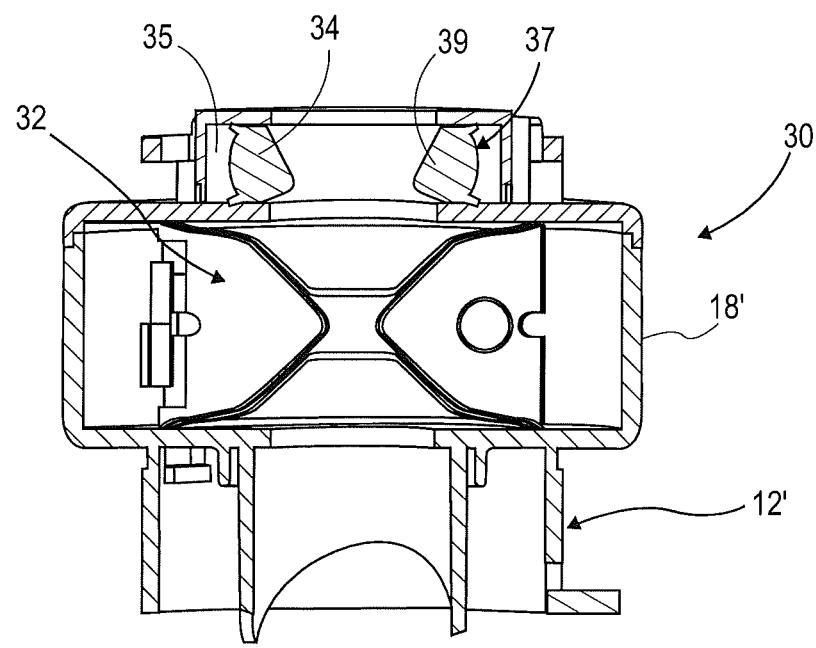
FIG. 2 is an interior, cross sectional view of a preferred embodiment of the seal assembly of the present invention.

FIG. 2 represents a preferred embodiment of the present invention and comprises the seal assembly 30 mounted within an appropriate portion of the trocar housing 12' and/or end portion 18'. Further, the various sealing components of the seal assembly 30 will be mounted along and at least partially define the intended path of travel of an instrument as it passes into and through the trocar 10 or 10'. Therefore the seal assembly 30 comprises a caged seal assembly generally indicated as 32 which may be used independently but preferably in combination with a supplementary or additional seal assembly generally indicated as 34.

Figure 2A:
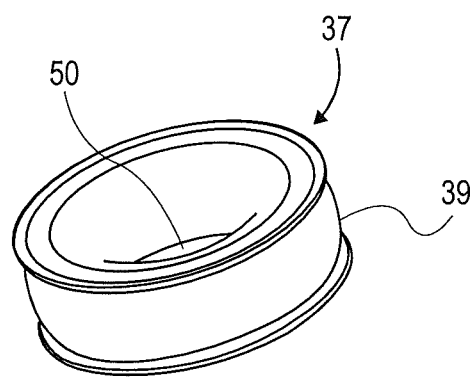
FIG. 2A is a perspective view one type of seal structure which may be incorporated, at least in part, in the various components of the seal assembly as represented in FIG. 2.
Figure 2B:
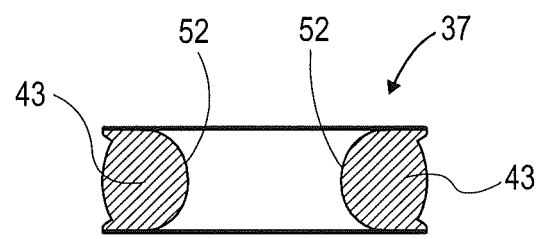
FIG. 2B is a sectional view of an embodiment generally similar to that of FIG. 2A.

With reference to FIGS. 2, 2A and 2B, the additional or supplementary seal assembly 34 is movably or "floatingly" disposed along the path of instrument travel within the interior of a compartment or cavity generally indicated as 35. One example of the supplementary seal assembly is disclosed in FIGS. 2A and 2B, and may include a single seal component generally indicated as 37 having a body portion 39 having an elastic material base 43 disposed in surrounding relation to a central channel generally indicated as 50. Upon entry into the trocar 10 and/or 10', an instrument passes along the aforementioned path of instrument travel and through channel 50. The base 43 and the channel 50 include interior surfaces 52, which are disposed, configured and dimensioned to sealingly engage any of a plurality of instruments which have a sufficiently large transverse dimension.

As will also be explained in greater detail, the structuring of the seal component 39 of the supplementary seal assembly 34 is such to accommodate, through the establishment of sealing engagement with instruments, a specifically larger dimensional range than that of the caged seal assembly 32. The structuring of the caged seal assembly 32 and the supplementary seal assembly 34, 39 to accommodate instruments of different dimensional ranges is important to the versatility and functioning of the seal assembly 30. Such versatility is further enhanced by the substantially inline relation of the caged seal assembly 32 and the supplementary seal assembly 34, 39 to one another relative to the intended path of travel of an instrument passing through the trocar 10 and/or 10'. Moreover, because of this specific inline alignment, the caged seal assembly 32 and the supplementary seal assembly 34, 39 may be considered to be at least partially or temporarily disposable in coaxial alignment with one another and with a central longitudinal axis of the housing 12' and/or end portion 18', even though both of these seal assemblies are movable in a floating manner, as described in greater detail in a currently pending U.S. patent application, namely, Ser. No 11/375,540 filed on Mar. 14, 2006, and its parent application, namely, Ser. No. 10/424, 564 filed on Apr. 28, 2003 which matured into U.S. Pat. No. 7,011,314, both by the inventor herein, and both of these documents being incorporated herein in their entirety by reference.

Figure 3:
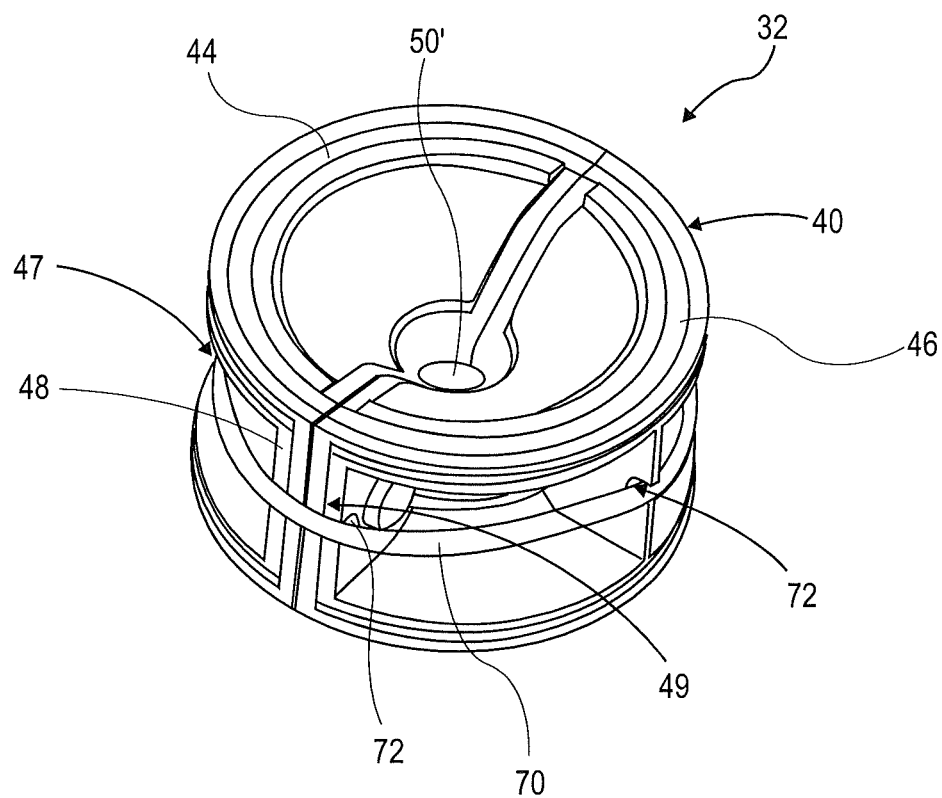
FIG. 3 is a rear perspective view of a caged seal assembly, disposed in a sealing orientation and which may define a portion of the embodiment of FIG. 2 and/or may further define an embodiment to be used independently.
Figure 4:
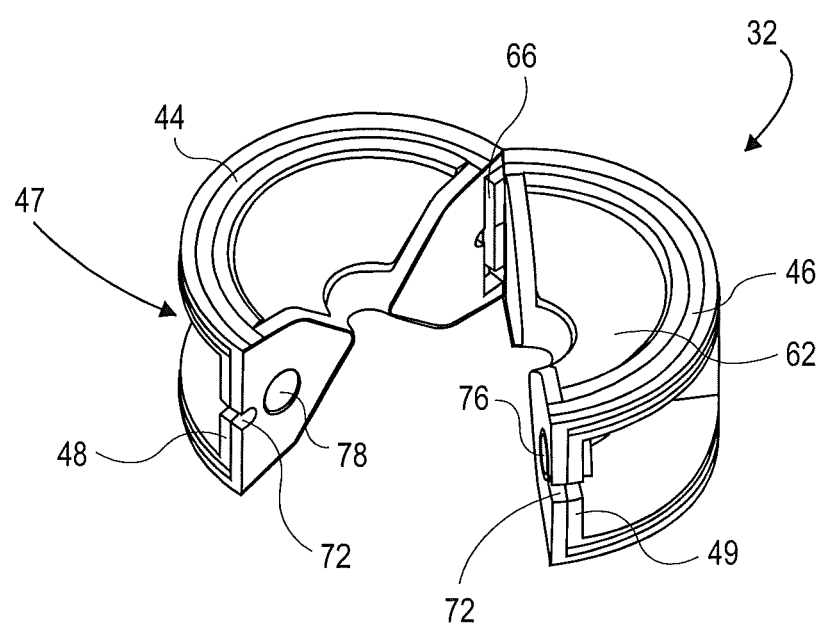
FIG. 4 is a perspective view of the preferred embodiment of FIG. 3 disposed in a non-sealing orientation.

With primary reference to FIGS. 3 and 4, the caged seal assembly 32 comprises a seal structure 40 which includes or is defined by a plurality of preferably two seal segments 44 and 46. The seal segments 44 and 46 are disposable between a sealing orientation as represented in FIG. 3, and an open, separated, non-sealing orientation as represented in FIG. 4. As should be apparent, the sealing orientation of FIG. 3 comprises the seal segments 44 and 46 being in a "closed" position relative to one another such that the seal segments 44 and 46 collectively surround and establish sealing engagement with an instrument passing into and through the central channel 50'. Accordingly, when the seal segments 44 and 46 are in a sealing orientation, the relatively closed positioning thereof allows the seal structure 40 to function substantially the same as the schematically represented seal member disclosed in FIGS. 2A and 2B. However, the obvious distinguishing features are that the seal segments 44 and 46 are separable and/or detachable from one another.

As set forth above, the caged seal assembly 32 may be used independently of the additional or supplementary seal assembly 34, 39. However, a preferred embodiment of the seal assembly 30 as represented in FIG. 2 comprises a combination of the caged seal assembly 32 disposed in substantially in-line relation with the supplementary seal assembly 34, 39. However, when utilized separately or independently, the caged seal assembly 32 may define yet another preferred embodiment structured to be operatively disposed in the housing 12 and/or 12' or other appropriate portion of the trocar in order to establish the intended sealing engagement with an instrument passing therethrough.

Figure 5A:
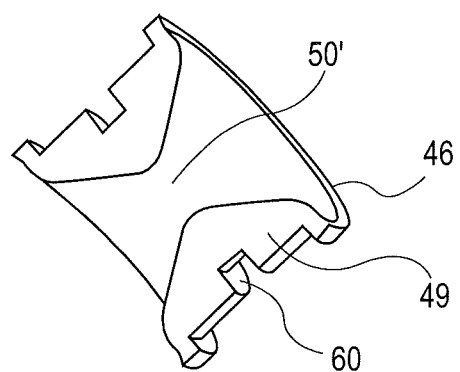
FIG. 5A is a perspective view of one seal segment associated with the preferred embodiments of FIGS. 3 and 4.
Figure 5B:
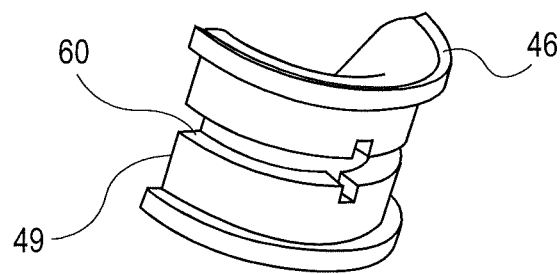
FIG. 5B is another perspective view of the seal segment embodiment of FIG. 5A.

Further, with regard to FIGS. 3 and 4, the caged seal assembly 32 also includes a cage structure 47 comprising two cage segments 48 and 49. Each of the cage segments 48 and 49 are connected to different ones of the seal segments 44 and 46 such that movement of the seal segments 44 and 46 corresponds with movement of the connected ones of the cage segments 48 and 49. As represented in FIGS. 5A and 5B, each of the seal segments 44 and 46 may be equivalently dimensioned, configured and structured.

Accordingly, the physical description of one of the segments as at 44 will be representative of both of the seal segments 44 and 46. Therefore, each of the seal segments includes or defines one half or other appropriate portion of the central channel as at 50'. However, the exterior of each of the seal segments 44 and 46 are cooperatively dimensioned and configured to facilitate the stable connection of a corresponding one of the cage segments 48 and 49.

More specifically, and as an example of one potential embodiment, the exterior portions of each of the seal segments 44 and 46 include a curvilinear groove or recessed portion 60 designed to receive and become interconnected to an inwardly directed curvilinear flange 62 formed on the interior surface of each of the cage segments 48 and 49. The respective flanges 62 are dimensioned and configured to be received within and establish a firm, a stable connection with the groove 60.

Accordingly, both the cage segments 48 and 49 are connected to and move with the corresponding seal segments 44 and 46, as the seal segments 44 and 46 move between the sealing orientation of FIG. 3 and the non-sealing orientation of FIG. 4.

Figure 6:
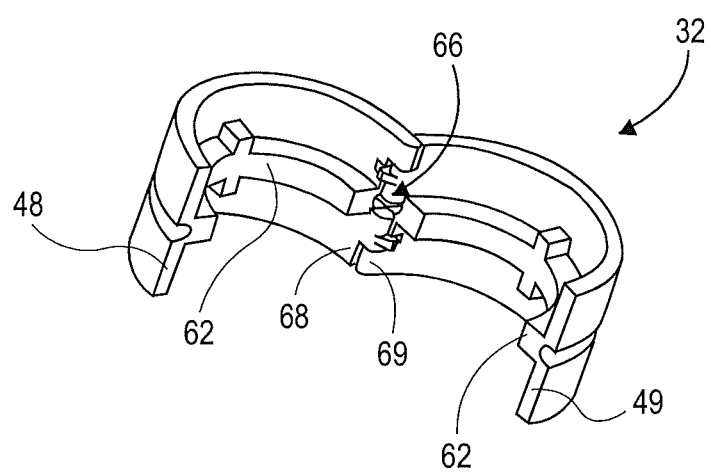
FIG. 6 is a perspective interior view of a cage structure associated with and defining at least a part of the embodiments of FIGS. 2-4.
Figure 6A:
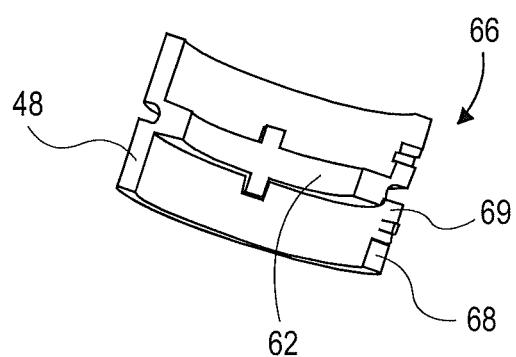
FIG. 6A is an interior perspective view of one cage segment associated with the embodiment of FIG. 6.
Figure 6B:
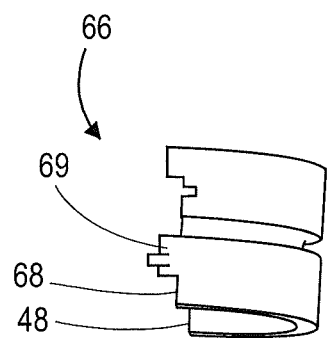
FIG. 6B is an exterior perspective view of the cage segment represented in FIG. 6A.
Figure 7:
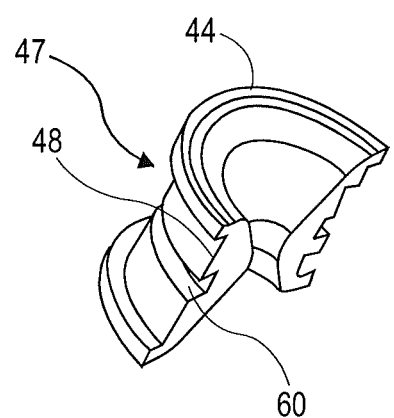
FIG. 7 is a perspective view showing both interior and exterior portions of a seal segment.

FIGS. 6, 6A, and 6B disclose the details of a hinge structure generally indicated as 66, which pivotally and/or removably connects the cage segments 48 and 49. Accordingly, the hinge structure 66 allows relative movement of the cage segments 48 and 49, along with corresponding ones of the seal segments 44 and 46, into and out of the sealing orientation of FIG. 3 and the non-sealing orientation of FIG. 4.

More specifically, in comparing the cage segments 48 and 49 as represented in FIGS. 6A, and 6B, the hinge structure 66 includes a locking or pivoting lug 68 and a receiving groove 69 formed on one of the cage segments 48. Both the lug 68 and the groove 69 are disposed and dimensioned to receive a corresponding groove and lug respectively formed on the opposite or cooperatively structured cage segment 49. As such, the cage segments 48 and 49 as well, as the seal segments 44 and 46 connected thereto, can be disposed between the sealing orientation of FIG. 3 and the non-sealing orientation of FIG. 4. Additional well known hinge structures could also be used, employing hinge elements and hinge pins as understood by those of skill in the art.

As set forth above, the non-sealing orientation of FIG. 4 is assumed by a "forced" opening or separation of the seal segments 44 and 46 about the hinge structure 66 when a "large" instrument attempts to pass through the caged seal assembly 32 as by passing through the central channel 50'.

Such a large instrument is generally defined as an instrument having a larger transverse or outer dimension than the predetermined dimensional range for which the caged seal assembly 32 was designed. As an example, this will probably be an instrument having an outer diameter larger than about 6 mm. although this should not be taken in a limiting sense.

Figure 8:
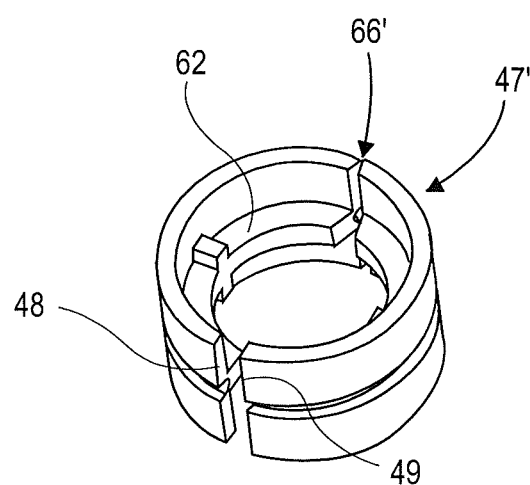
FIG. 8 is a perspective view of yet another embodiment of a cage structure which may be utilized with the embodiments of FIGS. 2 and 3.

Alternatively, and with primary reference to FIG. 8, another preferred embodiment of the caged seal assembly 32, which also may be incorporated within the preferred embodiment of the seal assembly 30 of FIG. 2, comprises the caged structure 47' including a plurality of preferably two cage segments 48 and 49 being integrally connected and/or formed as a one piece construction by virtue of an integral hinge structure generally indicated as 66'. More specifically, the hinge structure 66' is integrally connected to both the cage segments 48 and 49 and integrally formed with the cage structure 47' as shown. While the cage segments 48 and 49 are both formed from a substantially rigid material, the dimension and configuration of the integral hinge structure 66' is such as to facilitate the movable and/or pivotal interconnection of the cage segments 48 and 49 into and out of either the sealing orientation of FIG. 3 or the non-sealing orientation of FIG. 4. This integral hinge structure 66' is and/or should be a viable alternative to the lug and groove hinge structure 66, as described with reference to FIGS. 6, 6A, 6B.

As set forth above, one structural and operative feature of the various preferred embodiments of the present invention, including the preferred embodiment represented in FIG. 2, is that the caged seal assembly 32 can be said to be "automatically" disposable between the sealing orientation and the non-sealing orientation. More specifically, when a larger instrument having a transverse dimension greater than the predetermined dimensional range for which the caged seal assembly 32 was designed is forced through the central channel 50', the seal segments 44 and 46 will be forced into a separated or open, non-sealing orientation as represented in FIG. 4. However upon the removal of the larger instrument, the caged seal assembly 32 will automatically assume the sealing orientation of FIG. 3 due to the provision of a biasing assembly associated with each of the preferred embodiments of the caged assembly 32.

More specifically, and in a first embodiment, the caged seal assembly 32 includes the biasing assembly comprising a spring like biasing member. With primary reference to FIG. 3, the biasing member of at least one embodiment of the biasing assembly comprises what may generally be referred to as an O-ring. This elastic material bias or spring member 70 is disposed within an annular or other curvilinear groove or channel 72 formed on the exterior of each of the cage structures 47 and/or 47' and more specifically on each of the cage segments 48 and 49. While not clearly represented in FIG. 4, the biasing annularly configured O-ring type of spring or biasing member 70 is of a one piece construction and is disposed in surrounding relation to the cage structure 47 or 47'. Upon an attempted or forced opening or separation of the cage segments 48 and 49 so as to assume the non sealing orientation, the elastic spring or biasing member 70, will expand to the extent of allowing a "larger" instrument to pass through the central channel 50' without undue drag or frictional resistance being applied thereto. However upon a removal of the larger instrument, the spring or biasing member 70 will force the cage segments 48 and 49 into the closed orientation represented in FIG. 3. Accordingly, the seal segments 44 and 46 will also automatically be biased back into the sealing orientation of FIG. 3. Therefore, it should be apparent that the dimension, configuration and disposition of the spring or biasing member 70, defining at least one preferred embodiment of the biasing assembly is such as to normally bias the cage structure 47 into a closed position such that the seal segments 44 and 46 assume the aforementioned sealing orientation.

Figure 9:
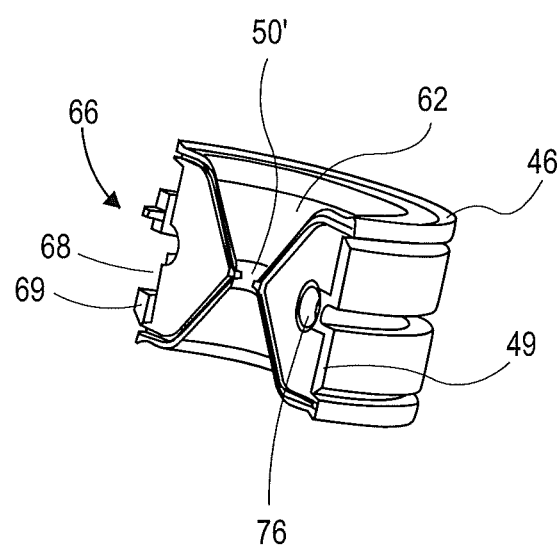
FIG. 9 is a perspective interior view of one embodiment of a biasing assembly which may be associated with either of the preferred embodiments of FIGS. 2 and 3.

Yet another preferred embodiment of the biasing assembly is shown in detail in FIG. 9 and is represented at least partially schematically in FIGS. 4 and 6. More specifically, the biasing assembly of the embodiment of FIGS. 4, 6 and 9 comprises a magnetic coupling including cooperatively disposed and structured magnetic members 76 and 78. The magnetic members 76 and 78 are disposed appropriately on each of the cage segments 48 and 49 as best represented in FIG. 4. More specifically, the magnetic members 76 and 78 are attracted to one another due to the proper structuring of their respective magnetic poles. As such, the disposition and structure of the cooperating magnetic members 76 and 78 are such as to normally bias the cage segments 48 and 49 into a closed position such that the corresponding seal segments 44 and 46 are normally biased and eventually disposed into the seal orienting position of FIG. 3. The strength of the cooperating magnetic member 76 and 78 are such as to continue to bias the cage segments 48 and 49 into the closed position even when they are separated or opened, such as when they are forced into the non sealing orientation of FIG. 4 by a large instrument passing through the caged seal assembly 32. Therefore, the biasing assembly comprising the magnetic members 76 and 78 can be said to find a magnetic coupling structure which normally biases the caged structure 47 into a closed position such that the seal segments 44 and 46 are normally biased into the sealing orientation. The biasing force is relatively weak when the seal structure is open. The opposed magnets 76 and 78 provide a very strong biasing force when the seal structure is closed, which helps keep the seal from opening when a larger of a small set of instruments is inserted. When the seal is opened by insertion of a even larger instrument, the biasing force is weak, which helps keep the drag on larger instruments low.

Referring now to FIGS. 10-14, there is shown another preferred embodiment of a caged seal assembly, generally indicated as 80, in accordance with the present invention. As before, the caged seal assembly 80 may be mounted in an appropriate portion of the trocar housing 12' and/or end portion 18' and, when utilizing the caged seal assembly 80, various sealing components of the seal assembly 30 will be substantially the same as represented in FIG. 2, at least to the extent that the seal assembly 30 will be mounted along and at least partially define the intended path of travel of an instrument as it passes into and through the trocar 10 or 10'. Therefore, in this preferred embodiment, the seal assembly 30 includes the caged seal assembly 80 which, as set forth above, may be used independently of, but preferably in combination with, a supplementary seal assembly generally indicated as 34, 39 in FIG. 2. Also similar to the embodiment of FIG. 2, the supplementary seal assembly 34, 39 is movably or "floatingly" disposed along the path of the instrument travel within the interior of a compartment or cavity, generally indicated as 35 of the trocar portion 12'. As also described above, the structuring of the seal component 39 of the supplementary seal assembly 34 is such as to accommodate a significantly larger dimensional range of medical instruments than that of the caged seal assembly 80.

As a result, the cooperative structuring of the caged seal assembly 80 and the supplementary seal assembly 34 is to accommodate instruments of different dimensional ranges thereby adding to the operative versatility and functioning of the seal assembly 30 whether the caged seal assembly 80 or 32 is utilized. Moreover, because of this specific in-line alignment, the caged seal assembly 80 and the supplementary seal assembly 34 may be considered to be at least partially or temporarily disposable in co-axial alignment with one another and with the central longitudinal axis of the housing of the trocar 12' and/or end portion 18'. This partially or at least temporarily disposed co-axial alignment is possible even though both of the supplementary seal assembly 34 and the caged seal assembly 80 are movable in a floating manner as described in greater detail in the aforesaid currently pending U.S. patent application Ser. No. 11/375,540 and U.S. Pat. No. 7,011,314 B2 to the inventor herein.

Figure 10:
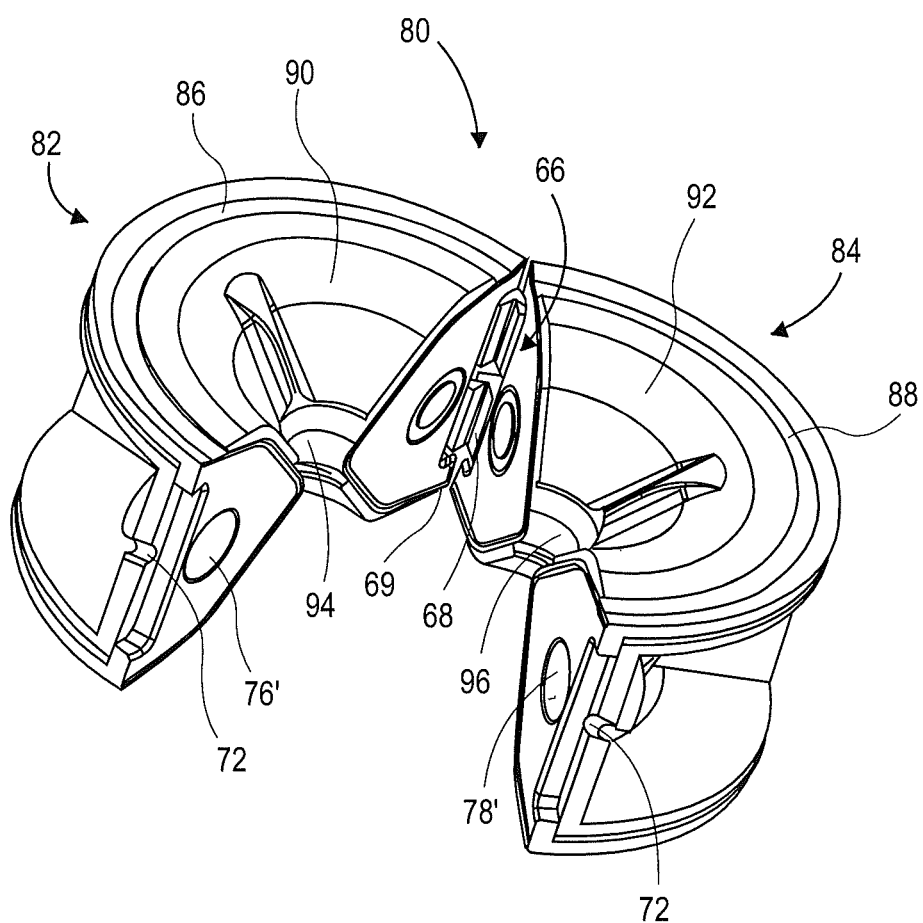
FIG. 10 is a front perspective view of another preferred embodiment of a caged seal assembly in an open or non-sealing orientation functionally similar to but structurally distinguishable from the embodiment of FIGS. 3-4.
Figure 11:
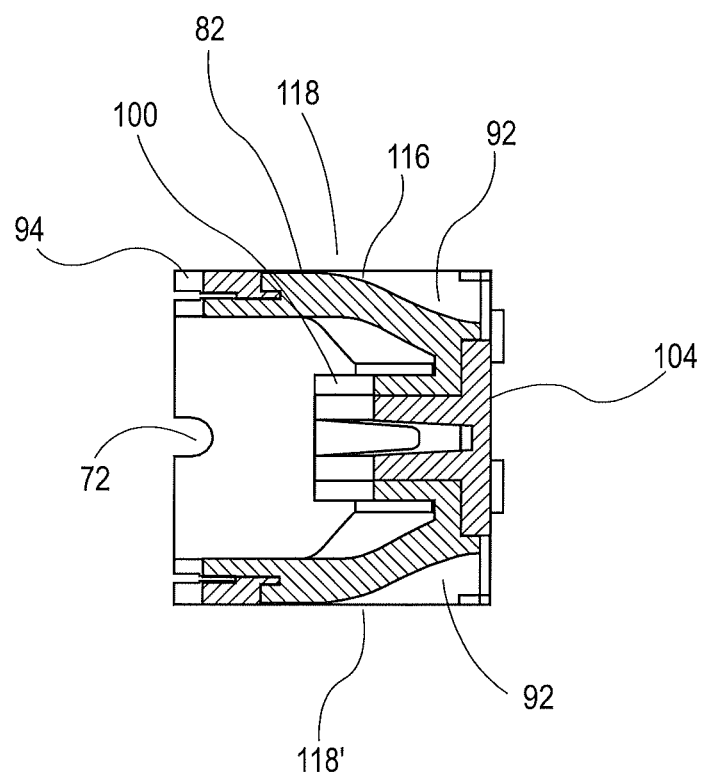
FIG. 11 is a sectional view of a portion of the caged seal assembly of the embodiment of FIG. 10.
Figure 12:
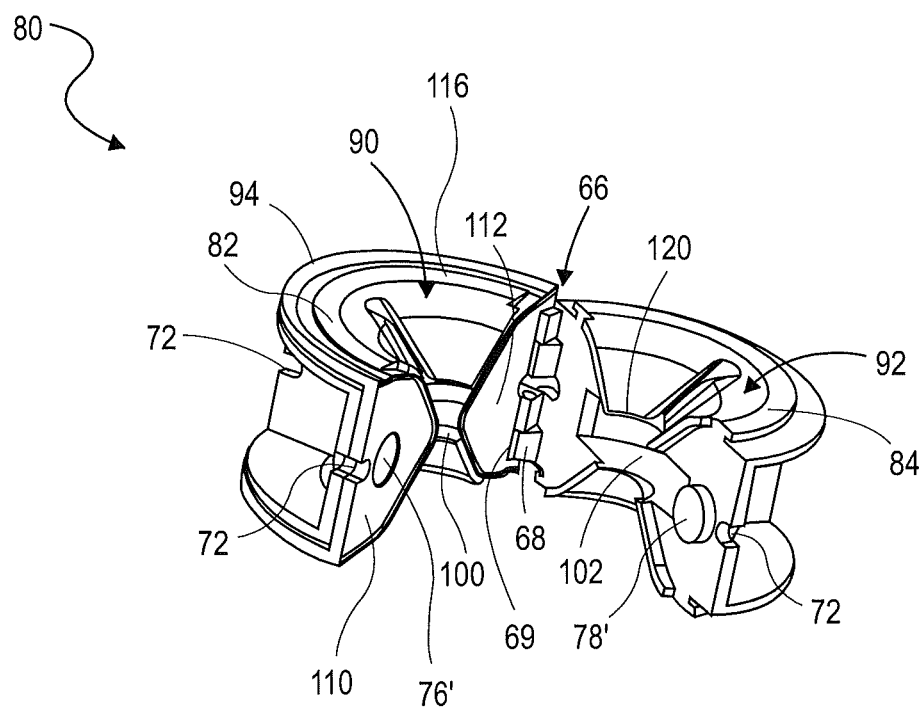
FIG. 12 is a front perspective view of a partially assembled cage seal assembly of the embodiment of FIGS. 10 and 11.
Figure 13:
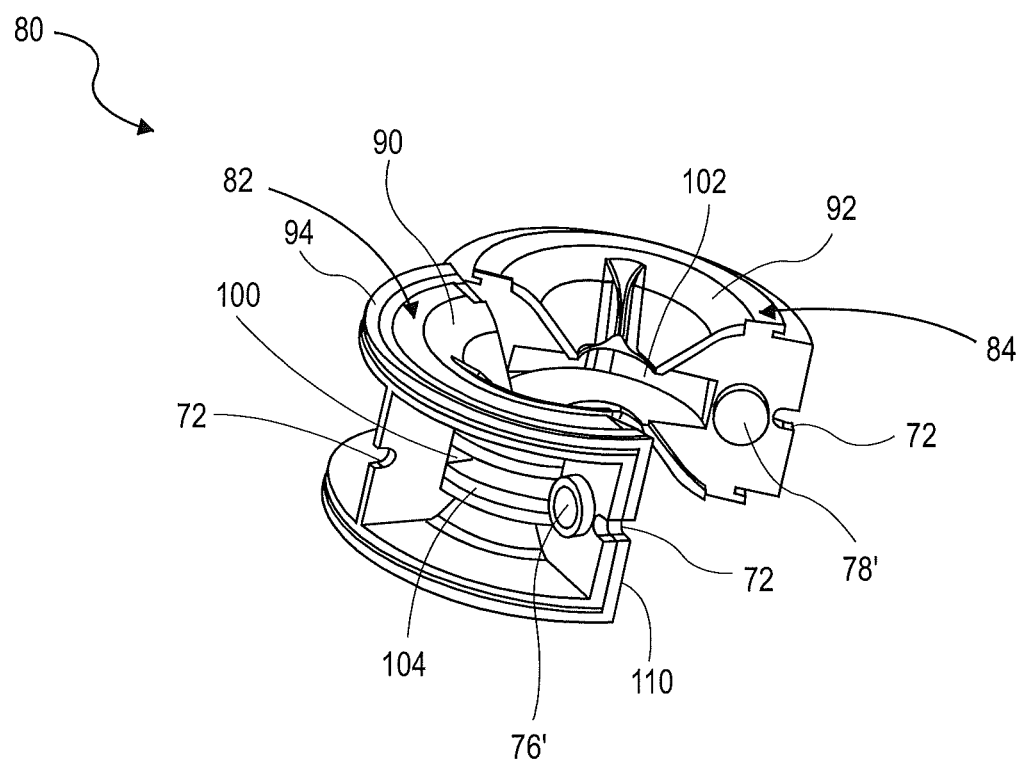
FIG. 13 is a side perspective view of a partially assembled cage seal assembly of the embodiment of FIGS. 10-12.
Figure 14:
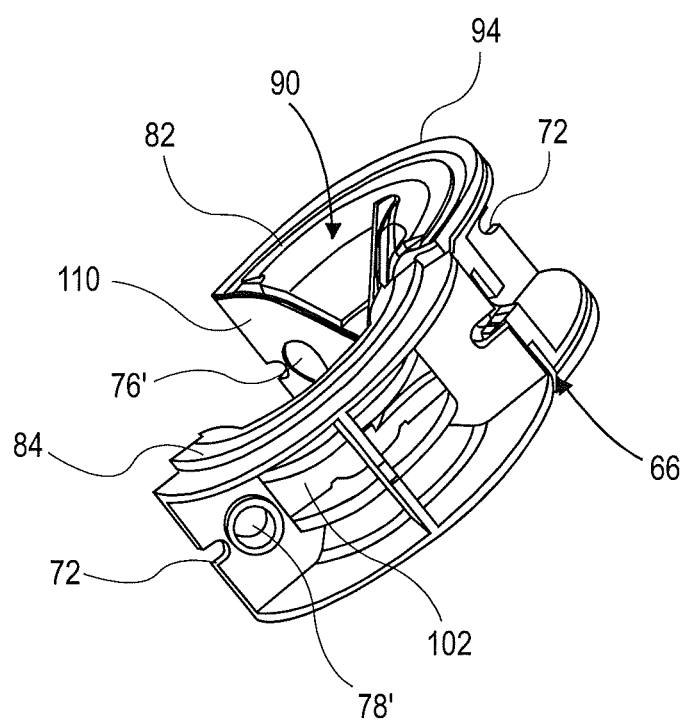
FIG. 14 is an opposite side perspective view of the embodiment of FIG. 13.

Accordingly, structural details specifically associated with the additional preferred embodiment of the caged seal assembly 80 are represented in FIGS. 10-14, wherein the caged seal assembly includes a cage structure comprising a plurality of preferably two cage segments 82 and 84, as well as a plurality of two seal segments 86 and 88. For purposes of clarity, the embodiments of the caged seal assembly 80 as represented in FIGS. 12-14 are only partially assembled, thereby facilitating the detailed description of each of the cage segments 82 and 84, as well as their corresponding seal segments 86 and 88.

As with the embodiment of FIG. 3, each of the cage segments 82 and 84 are movably connected to one another by a hinge assembly 66, described in greater detail in FIGS. 6, 6A, 6B. Moreover, the hinge 66 may include the lug 68, 68' and groove 69, 69' construction, or alternately may include the integral hinge 66' as represented in FIG. 8, or a hinge-pin design. Regardless of the specific hinge or like coupling structure 66 or 66' utilized, the cage segments 82 and 84, as well as the corresponding seal segments 86 and 88, are movable relative to one another between a closed, sealing orientation similar to the sealing orientation of the embodiment of FIG. 3 and/or an open, non-sealing orientation as represented in FIG. 10.

Also present in the embodiment of the caged seal assembly 32 as represented in FIG. 3, the caged seal assembly 80 includes a biasing assembly connected to or otherwise associated with one or both of the cage segments 86 and 88. More specifically, the biasing assembly may assume the equivalent structure of a biasing member in the form of an annular member or "O-ring" formed of a sufficiently elastic material to allow the cage segments 82 and 84 and their corresponding seal segments 86 and 88 to be forced into an at least minimally open, non-sealing orientation. The biasing member 70 is secured to both of the cage segments 82 and 84 by being disposed within a plurality of spaced apart slots or grooves 72 which collectively form a retaining channel or like structure in which the biasing spring or member 70 may be secured. Metallic spring member of various designs could also be incorporated.

Alternatively and/or in combination with the spring-like biasing member 70, the biasing assembly may also include a magnetic coupling including magnetic coupling components 76' and 78' similar to those described in detail with the above noted caged seal assembly 32 as with specific reference to FIGS. 4 and 9.

This embodiment of the caged seal assembly 80 includes the provision of a guide assembly, and preferably, a guide assembly defined by a plurality of preferably two guide segments 90 and 92. In this embodiment, as illustrated, each of the guide segments 90 and 92 are defined by integral or fixed portions of corresponding ones of cage segments 82 and 84. Further, the guide segments 90 and 92 are formed from a plastic or other appropriate material having a predetermined, sufficient degree of rigidity so as to facilitate the guiding of an instrument as it enters the caged seal assembly 80 and passes through the sealing portions 94 and 96 of the respective seal segments 86 and 88. More specifically, the at least partially rigid material from which the guide segments 90 and 92 are formed are also sufficiently rigid to prevent the cutting, gauging, penetration or other serious deformation of the exposed surfaces of the guide portions 90 and 92. This predetermined degree of rigidity further facilitates the efficient positioning or manipulation of the instrument passing into and through the caged seal assembly 80 by preventing or at least significantly restricting the tendency of the leading end of the instrument from indenting or otherwise being caught or "hung-up" on the interior of the cage assembly prior to it entering the sealing portions 94 and 96.

In contrast, it should be appreciated that the material from which sealing segments 86 and 88 and in particular the sealing portions 94 and 96 thereof are sufficiently flexible and/or resilient to establish an efficient, reliable sealing engagement with the outer surfaces of the instrument when the caged seal assembly 80 is in the closed or sealing orientation as represented with the embodiment of FIG. 3.

As set forth in detail above, and as more fully described hereinafter, the dimension and configuration of the sealing segments 86 and 88 and in particular the respective sealing portions 94 and 96, when the caged seal assembly 80 is in the closed or sealing orientation is such as to allow the passage therethrough of instruments having a size which is substantially within a "predetermined dimensional range." When an instrument falling within this predetermined dimensional range passes through the caged seal assembly 80 when the caged seal assembly is in the closed or sealing orientation, the sealing portions 94 and 96 are cooperatively disposed, configured and structured to substantially surround the passing instrument and establish a substantially fluid tight seal with the outer surfaces thereof.

Accordingly, the versatility of the seal assembly which incorporates both the caged seal assembly 80 and the supplementary seal assembly 34 is significantly enhanced by the virtue of the establishment of sealing engagement with the exterior surface of instruments having various sizes passing through the trocar 12', wherein the various sized instruments may have relatively small or relatively large dimensions. As emphasized above with the embodiment of FIGS. 2 and 3, the caged seal assembly 80 may be structured to establish sealing engagement with relatively small instruments such as, but not limited to, a dimensional range of generally about 3 mm to generally about 5 mm. However, during a typical laparoscopic surgical procedure the medical personnel may require the need or use of a significantly larger instrument such as, but not limited to, the dimensional range of generally about 9 mm to generally 15 mm. Utilization of a larger instrument having a dimensional range substantially larger than that intended for use with the caged seal assembly 80 would normally cause a significant drag or frictional engagement between the instrument and the sealing portions 94 and 96. This could possibly cause difficulty or inaccuracies as the instrument is manipulated by the medical personnel.

Problems of this type are overcome by the provision of the supplementary seal assembly 34 and the ability of the caged seal assembly 80 to "automatically" assume the non-sealing orientation or open orientation when a larger instrument outside of the aforementioned predetermined dimensional range is utilized. Moreover, supplementary seal assembly 34 is disposed, dimensioned and configured to establish sealing engagement with an instrument having the larger dimensional range such as, but not limited to, the aforementioned 10 mm to 15 mm range. Accordingly when a larger instrument is passed through the trocar 12', sealing engagement is established between the supplementary seal assembly 34 and the larger instrument. Further, when the larger instrument passes into and through the caged seal assembly 80, cooperatively structuring and disposition between the cage segments 82 and 84 and the biasing assembly, in its various embodiments, will allow an opening or separation of the two seal segments 86 and 88 and more specifically, an opening or a separation of the sealing portions 94 and 96 associated therewith. As such, the passage of the larger instrument will cause or "force" the two sealing portions 94 and 96 and their associated seal segments 86 and 88 out of the normal closed or sealing orientation. In addition, the provision of the guide segments 90 and 92 will further facilitate the passage of an instrument through the caged seal assembly 80, regardless of its size such that sealing of the instrument, passing through the caged seal assembly 80 will occur either by sealing engagement with the supplementary seal 34 or the caged seal assembly 80 and more specifically the sealing portions 94 and 96.

It should further be recognized that there may be a dimensional range of instruments that may be sealed by both the caged seal assembly 80 and the supplementary sealed assembly 34. The further regard to the examples described herein the dimensional range of such instruments would be somewhat larger than generally about 5 mm and somewhat smaller than generally about 10 mm.

Yet additional structural features clearly represented in FIGS. 10-14 which facilitate a firm, stable yet removable attachment of the respective seal segments 86 and 88 to corresponding ones of the caged segments 82 and 84 include an elongated, somewhat curved opening or aperture formed in each of the cage segments 82 and 84. These apertures are disposed, dimensioned and configured to receive outer or exterior portions of respective ones of the sealing portions 94 and 96. In addition, each of the cage segments 82 and 84 include oppositely disposed, spaced apart curvilinear flanges as at 100 and 102. Each of the flanges 100 and 102 of the respective seal segments 86 and 88 are cooperatively dimensioned and configured to receive curvilinear flanges 104 of the seal segments 86 and 88 in receiving relation to outer surfaces thereof. Further, the curvilinear flanges 100, 102, and 104 of the respective seal segments 84 and 86 are disposed, dimensioned and structured to establish a substantially fluid tight seal with correspondingly positioned interior surface portions of the trocar 12'.

In addition, each of the seal segments 86 and 88 include end panels 110 and 112 which are disposed in confronting, sealing engagement with one another when the caged seal assembly 80 is in the closed, sealing orientation. The cooperative disposition, configuration and dimension of the panels 110 and 112 of each of the sealing segments 86 and 88 facilitate the sealing portions 94 and 96 forming a fluid tight seal about the exterior surface of an appropriately sized instrument passing through the caged seal assembly 80.

Additional structural features of the caged seal assembly 80 include each of the guide sections 90 and 92 having an outer end 116 located adjacent to and/or contiguous with the entrance end 118 of the caged seal assembly 80, as best represented in FIG. 11. In addition, each of the guide segments 90 and 92 have a convergent configuration as they extend inwardly into an inner end 120. The inner ends 120 of each of the guide segments 90 and 92 are disposed adjacent to or immediately contiguous with the corresponding sealing portions 94 and 96. As such, non-interruptive passage of the instrument may be facilitated as it first engages one or both of the guide portions 90 and 92 and as it proceeds into a directed travel into and through the sealing portions 94 and 96 of the corresponding seal segments 86 and 88.

With further reference to FIG. 11, it is noted that the sealing portions 94 and 96 are located at a substantially midpoint location between the entrance end 118 and the exit end 118' of the corresponding cage segments 82 and 84. This midpoint location of the sealing segments 94 and 96 provides a symmetry which may facilitate manufacture and/or assembly in that the respective seal segments 86 and 88 may be placed within their cage segments 82 and 84 in either orientation such that the guide portions 90, 92 or 90', 92' may be disposed adjacent to what may be considered the entrance end 118 of the caged seal assembly 80.

However, in certain additional modifications contemplated within the spirit and scope of the present invention the sealing portions 94 and 96 may be off center and not at a midpoint location such as being closer to the exit end 118'. However, one possible disadvantage with this non symmetrical configuration would be requirement of a more detailed assembly such that the guide portions 90 and 92 would be located adjacent to or contiguous with the entrance end 118 and the guide portions 90', 92' would be located adjacent to and contiguous with the exit end 118' of the respective cage segments 82 and 84.

Figure 15:
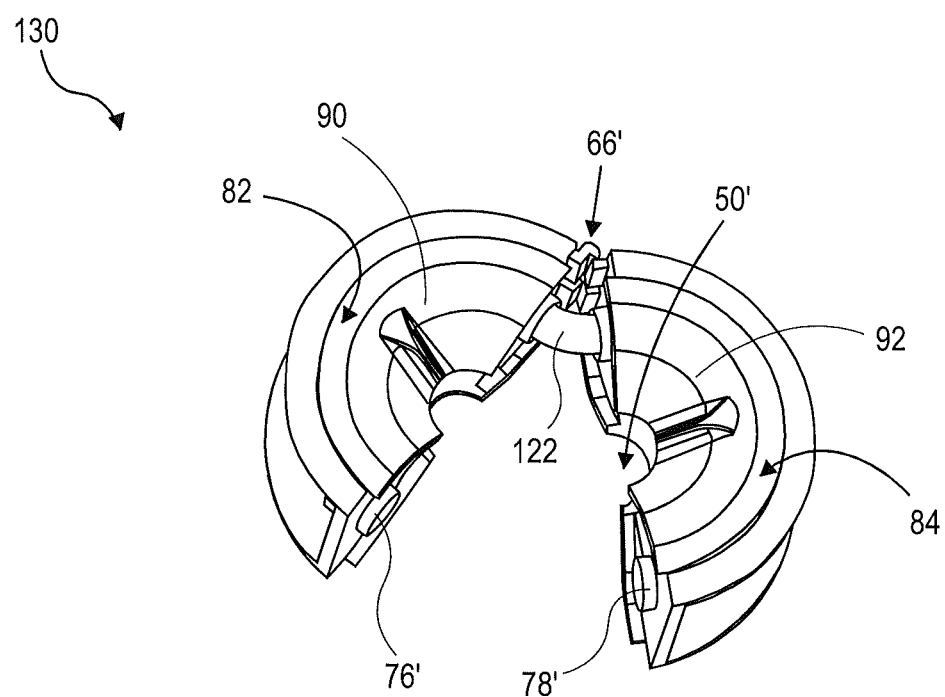
FIG. 15 is a front perspective view of an embodiment of a biasing assembly for use in a cage seal assembly.
Figure 16:
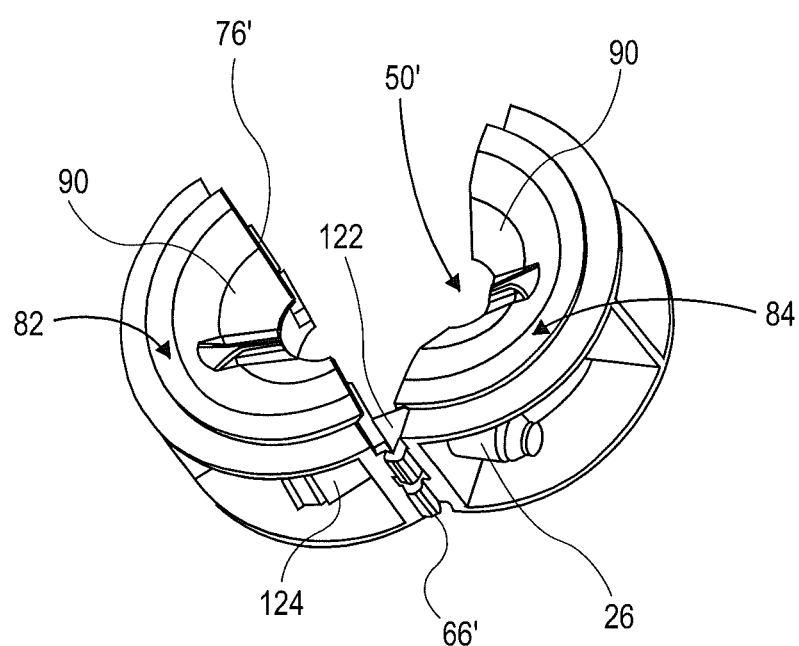
FIG. 16 is a rear perspective view of the embodiment of the biasing assembly illustrated in FIG. 15.
Figure 17:
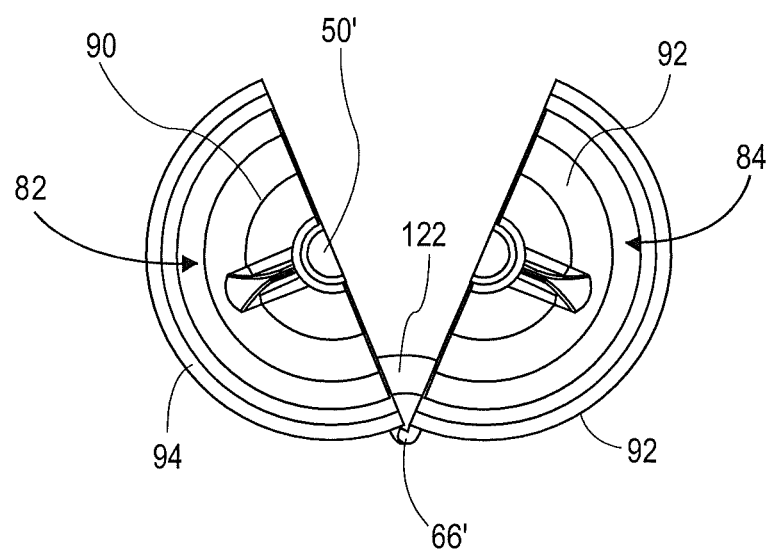
FIG. 17 is an aerial view of the embodiment of the biasing assembly illustrated in FIGS. 15 and 16.

FIGS. 15-17 illustrate perspective views of an embodiment of a biasing assembly for use in a cage seal assembly. Biasing member 122 is disposed between cage segment 82 and cage segment 84 of an embodiment of a caged seal assembly 130. The biasing member 122 is disposed such that when an instrument passing into the central channel 50' causes the central channel 50' to expand, the biasing member 122 allows the cage segments 82 and 84 to expand to allow the instrument to pass. Upon removal of the instrument the biasing member 122 also expands and will force the cage segments 82 and 84 back into a closed configuration. The biasing member 122 can be formed from an elastomeric material or any other material that has elastic properties, and includes respective ends 124 and 126 as shown in FIG. 16. Biasing member 122 is positioned to hold the seal structure mating faces closed and assures that hinge members 66 and/or 66' remain engaged during seal opening and closing. Upon insertion of a large instrument, the seal first opens at the magnet side, hinging at 66 and/or 66'. Biasing means 122 is strong enough to bring the seal halves back into the sealed position after removing larger instruments even if magnetic biasing is not present.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A seal assembly comprising;
   a first and second seal made of a resilient material, the first and second seals configured in series and oriented to receive an elongated instrument through an opening in a center section of each of the first and second seals,
   wherein the first seal is in a fixed annular configuration and the entire first seal is radially moveably disposed in the assembly and the second seal is moveably disposed in the assembly and the opening in the center section of the first seal has a larger diameter than the opening in the second seal; and
   wherein the second seal includes: a first caged segment and a second caged segment, the first caged segment and the second caged segment together forming an annularly shaped body having the opening in a center portion the body, and a hinge portion configured to allow the first caged segment and the second caged segment of the annulary shaped body to open to form a C shape.

2. The seal assembly of claim 1, wherein the opening of the first seal and the opening of the second seal are dimensioned so that the first seal creates a seal around an outer diameter of an elongated object inserted into the seal assembly if the outer diameter is within a first range and the second seal creates a seal if the outer diameter of the elongated object when the outer diameter is within a second range.

3. The seal assembly of claim 1, wherein the first seal assembly is in the shape of an annulus having interior portions made of an elastic material.

4. The seal assembly of claim 3, wherein the interior portions are configured to engage a rod-shaped object of a given diameter in a substantially fluid tight manner.

5. The seal assembly of claim 1, wherein the second seal includes a biasing element configured to bias the body to a closed annular shape.

6. The seal assembly of claim 5, wherein the biasing element includes a resilient member contained at least in part of each of the first caged segment and the second caged segment of the annularly shaped body.

7. The seal assembly of claim 5, wherein the biasing element includes a magnet.

8. The seal assembly of claim 5, further comprising a resilient outer portion attached to an outer surface of the annularly shaped body and configured to form a seal with a wall of a container containing the seal.

9. A seal assembly comprising:
   a first and second seal made of a resilient material, the first and second seals configured in series and oriented to receive an elongated instrument through an opening in a center section of each of the first and second seals, and
   wherein the first seal is in a fixed annular configuration and is moveably disposed in the assembly and the second seal is moveably disposed in the assembly and the opening in the center section of the first seal has a larger diameter than the opening in the second seal;
   wherein the second seal includes:
   an annularly shaped body having the opening in a center portion the body being formed of two members;
   a resilient inner portion about the circumference of the opening;
   a hinge portion configured to allow the two members of the body to open to form a C shape; and
   a biasing element configured to bias the body to a closed annular shape.

10. The seal assembly of claim 9, wherein the biasing element includes a resilient member contained at least in part of each of the two members of the body.

11. The seal assembly of claim 9, wherein the biasing element includes a magnet located in each of the two members of the body.

12. The seal assembly of claim 9, further comprising a resilient outer portion attached to an outer surface of the annularly shaped body and configured to form a seal with a wall of a container containing the seal.

13. The seal assembly of claim 9, wherein the first and second openings in the first and second seals are dimensioned so that the first seal creates a seal around an outer diameter of an elongated object inserted into the seal assembly if the outer diameter is within a first range and the second seal creates a seal if the outer diameter of the elongated object when the outer diameter is within a second range.

14. The seal assembly of claim 9, wherein the first seal assembly is in the shape of an annulus having interior portions made of an elastic material.

15. The seal assembly of claim 14, wherein the interior portions are configured to engage a rod-shaped object of a given diameter in a substantially fluid tight manner.

\* \* \* \* \*